(12) United States Patent
Pipenhagen et al.

(10) Patent No.: US 8,568,445 B2
(45) Date of Patent: Oct. 29, 2013

(54) EXTRA-VASCULAR SEALING DEVICE AND METHOD

(75) Inventors: Catherine A. Pipenhagen, Chanhassen, MN (US); Melissa K. Gardner, Mendota Heights, MN (US); William Fiehler, Exton, PA (US); Janet L. Jacobsen, Maple Grove, MN (US); Gary J. Schorr, Apple Valley, MN (US); Jyue Boon Lim, New Brighton, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1304 days.

(21) Appl. No.: 11/842,509

(22) Filed: Aug. 21, 2007

(65) Prior Publication Data
US 2009/0054926 A1    Feb. 26, 2009

(51) Int. Cl.
*A61B 17/08* (2006.01)
(52) U.S. Cl.
USPC .......................................................... 606/213
(58) Field of Classification Search
USPC .................................................. 606/213–216
See application file for complete search history.

(56) References Cited

U.S. PATENT DOCUMENTS

| | | | |
|---|---|---|---|
| 3,405,083 A | 10/1968 | Morrison et al. |
| 4,317,445 A | 3/1982 | Robinson |
| 4,744,364 A | 5/1988 | Kensey |
| 4,890,612 A | 1/1990 | Kensey |
| 5,021,059 A | 6/1991 | Kensey et al. |
| 5,055,410 A | 10/1991 | Blumenthal et al. |
| 5,061,274 A | 10/1991 | Kensey |
| 5,108,421 A | 4/1992 | Fowler |
| 5,192,302 A | 3/1993 | Kensey et al. |
| 5,222,974 A | 6/1993 | Kensey et al. |
| 5,282,827 A | 2/1994 | Kensey et al. |
| 5,290,310 A | 3/1994 | Makower et al. |
| 5,292,332 A | 3/1994 | Lee |
| 5,304,184 A | 4/1994 | Hathaway et al. |
| 5,306,254 A | 4/1994 | Nash et al. |
| 5,312,435 A | 5/1994 | Nash et al. |
| 5,320,639 A | 6/1994 | Rudnick |
| 5,326,350 A | 7/1994 | Li |
| 5,334,216 A | 8/1994 | Vidal et al. |
| 5,342,393 A | 8/1994 | Stack |
| 5,352,216 A | 10/1994 | Shiono et al. |

(Continued)

FOREIGN PATENT DOCUMENTS

| | | |
|---|---|---|
| WO | 03094749 | 11/2003 |
| WO | 2004041122 | 5/2004 |
| WO | 2007044510 | 4/2007 |

*Primary Examiner* — Gregory Anderson
(74) *Attorney, Agent, or Firm* — Holland & Hart

(57) ABSTRACT

Various embodiments of a device are shown and disclosed for closing a vascular access puncture site following percutaneous diagnostic or therapeutic interventional procedures. In one embodiment, the closure device includes a vessel locating member, an anchor and a sealing material. The closure device may be configured to deploy the anchor and the sealing material outside of a hole in a blood vessel to close the hole. The vessel locating member may be used to locate the blood vessel to ensure that the anchor and/or the sealing material are properly placed adjacent to the hole. The closure device may also include a tamper member configured to push or tamp the sealing material against the anchor. The closure device may also include a suture that is used to hold the sealing material and the anchor together adjacent to the hole in the blood vessel.

18 Claims, 12 Drawing Sheets

(56) References Cited

U.S. PATENT DOCUMENTS

| | | |
|---|---|---|
| 5,368,601 A | 11/1994 | Sauer et al. |
| 5,370,660 A * | 12/1994 | Weinstein et al. ............ 606/215 |
| 5,383,896 A | 1/1995 | Gershony et al. |
| 5,383,897 A | 1/1995 | Wholey |
| 5,383,899 A | 1/1995 | Hammerslag |
| RE34,866 E | 2/1995 | Kensey et al. |
| 5,391,183 A | 2/1995 | Janzen et al. |
| 5,403,328 A | 4/1995 | Shallman |
| 5,403,329 A | 4/1995 | Hinchcliffe |
| 5,405,354 A | 4/1995 | Sarrett |
| 5,411,520 A | 5/1995 | Nash et al. |
| 5,417,699 A | 5/1995 | Klein et al. |
| 5,431,639 A | 7/1995 | Shaw |
| 5,431,666 A | 7/1995 | Sauer et al. |
| 5,437,631 A | 8/1995 | Janzen |
| 5,443,481 A | 8/1995 | Lee |
| 5,462,561 A | 10/1995 | Voda |
| 5,486,195 A | 1/1996 | Myers et al. |
| 5,496,332 A | 3/1996 | Sierra et al. |
| 5,496,335 A | 3/1996 | Thomason et al. |
| 5,507,744 A | 4/1996 | Tay et al. |
| 5,507,758 A | 4/1996 | Thomason et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,571,181 A | 11/1996 | Li |
| 5,591,205 A | 1/1997 | Fowler |
| 5,593,422 A | 1/1997 | Muijs Van de Moer et al. |
| 5,601,603 A | 2/1997 | Illi |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,643,318 A | 7/1997 | Tsukernik et al. |
| 5,645,566 A | 7/1997 | Brenneman et al. |
| 5,649,959 A | 7/1997 | Hannam et al. |
| 5,653,730 A | 8/1997 | Hammerslag |
| 5,662,681 A | 9/1997 | Nash et al. |
| 5,665,106 A | 9/1997 | Hammerslag |
| 5,674,231 A | 10/1997 | Green et al. |
| 5,676,689 A | 10/1997 | Kensey et al. |
| 5,681,334 A | 10/1997 | Evans et al. |
| 5,700,277 A | 12/1997 | Nash et al. |
| 5,725,498 A | 3/1998 | Janzen et al. |
| 5,725,551 A | 3/1998 | Myers et al. |
| 5,728,122 A | 3/1998 | Leschinsky et al. |
| 5,728,132 A | 3/1998 | Van Tassel et al. |
| 5,728,133 A | 3/1998 | Kontos |
| 5,728,134 A | 3/1998 | Barak |
| 5,741,223 A | 4/1998 | Janzen et al. |
| 5,746,755 A | 5/1998 | Wood et al. |
| 5,755,727 A | 5/1998 | Kontos |
| 5,759,194 A | 6/1998 | Hammerslag |
| 5,766,183 A | 6/1998 | Sauer |
| 5,766,206 A | 6/1998 | Wijkamp et al. |
| 5,782,861 A | 7/1998 | Cragg et al. |
| 5,792,173 A | 8/1998 | Breen et al. |
| 5,807,573 A | 9/1998 | Ljusberg-Wahren et al. |
| 5,810,810 A | 9/1998 | Tay et al. |
| 5,810,846 A | 9/1998 | Virnich et al. |
| 5,810,884 A | 9/1998 | Kim |
| 5,814,065 A | 9/1998 | Diaz |
| 5,820,631 A | 10/1998 | Nobles |
| 5,827,299 A | 10/1998 | Thomason et al. |
| 5,830,130 A | 11/1998 | Janzen et al. |
| 5,843,124 A | 12/1998 | Hammerslag |
| 5,853,421 A | 12/1998 | Leschinsky et al. |
| 5,855,559 A | 1/1999 | Van Tassel et al. |
| 5,855,585 A | 1/1999 | Kontos |
| 5,860,990 A | 1/1999 | Nobles et al. |
| 5,861,004 A | 1/1999 | Kensey et al. |
| 5,861,005 A | 1/1999 | Kontos |
| 5,868,762 A | 2/1999 | Cragg et al. |
| 5,876,411 A | 3/1999 | Kontos |
| 5,902,311 A | 5/1999 | Andreas et al. |
| 5,906,631 A | 5/1999 | Imran |
| 5,910,155 A | 6/1999 | Ratcliff et al. |
| 5,919,207 A | 7/1999 | Taheri |
| 5,941,897 A | 8/1999 | Myers |
| 5,957,952 A | 9/1999 | Gershony et al. |
| 5,964,782 A | 10/1999 | Lafontaine et al. |
| 5,976,161 A | 11/1999 | Kirsch et al. |
| 5,980,539 A | 11/1999 | Kontos |
| 5,995,502 A | 11/1999 | Fukuda |
| 5,997,555 A | 12/1999 | Kontos |
| 6,007,562 A | 12/1999 | Harren et al. |
| 6,007,563 A | 12/1999 | Nash et al. |
| 6,017,359 A | 1/2000 | Gershony et al. |
| 6,024,747 A | 2/2000 | Kontos |
| 6,033,401 A | 3/2000 | Edwards et al. |
| 6,033,427 A | 3/2000 | Lee |
| 6,036,721 A | 3/2000 | Harren et al. |
| 6,042,601 A | 3/2000 | Smith |
| 6,045,569 A | 4/2000 | Kensey et al. |
| 6,048,357 A | 4/2000 | Kontos |
| 6,048,358 A | 4/2000 | Barak |
| 6,056,768 A | 5/2000 | Cates et al. |
| 6,063,085 A | 5/2000 | Tay et al. |
| 6,071,300 A | 6/2000 | Brenneman et al. |
| 6,077,279 A | 6/2000 | Kontos |
| 6,090,130 A | 7/2000 | Nash et al. |
| 6,110,184 A | 8/2000 | Weadock |
| 6,120,524 A | 9/2000 | Taheri |
| 6,126,675 A | 10/2000 | Shchervinsky et al. |
| 6,136,010 A | 10/2000 | Modesitt et al. |
| 6,139,556 A | 10/2000 | Kontos |
| 6,162,192 A | 12/2000 | Cragg et al. |
| 6,174,322 B1 | 1/2001 | Schneidt |
| 6,183,496 B1 | 2/2001 | Urbanski |
| 6,193,670 B1 | 2/2001 | Van Tassel et al. |
| 6,197,042 B1 | 3/2001 | Ginn et al. |
| 6,206,895 B1 | 3/2001 | Levinson |
| 6,228,383 B1 | 5/2001 | Hansen et al. |
| 6,231,561 B1 | 5/2001 | Frazier et al. |
| 6,245,080 B1 | 6/2001 | Levinson |
| 6,398,796 B2 | 6/2002 | Levinson |
| 6,425,911 B1 | 7/2002 | Akerfeldt et al. |
| 6,425,924 B1 | 7/2002 | Rousseau |
| 6,447,513 B1 | 9/2002 | Griggs |
| 6,508,828 B1 | 1/2003 | Akerfeldt et al. |
| 6,547,806 B1 | 4/2003 | Ding |
| 6,569,185 B2 | 5/2003 | Ungs |
| 6,596,012 B2 | 7/2003 | Akerfeldt et al. |
| 6,596,014 B2 | 7/2003 | Levinson et al. |
| 6,682,489 B2 | 1/2004 | Tenerz et al. |
| 6,695,867 B2 | 2/2004 | Ginn et al. |
| 6,712,837 B2 | 3/2004 | Akerfeldt et al. |
| 6,793,938 B2 | 9/2004 | Sankaram |
| 6,860,895 B1 | 3/2005 | Akerfeldt et al. |
| 6,890,343 B2 | 5/2005 | Ginn et al. |
| 6,929,655 B2 | 8/2005 | Engelov et al. |
| 7,850,654 B2 | 12/2010 | Belhe et al. |
| 2002/0082547 A1 | 6/2002 | Deniega et al. |
| 2003/0158577 A1 | 8/2003 | Ginn et al. |
| 2003/0171738 A1 | 9/2003 | Konieczynski et al. |
| 2004/0122349 A1 | 6/2004 | Lafontaine et al. |
| 2004/0172060 A1 | 9/2004 | Cates |
| 2004/0176800 A1 | 9/2004 | Paraschac et al. |
| 2004/0215232 A1 | 10/2004 | Belhe et al. |
| 2005/0085854 A1 | 4/2005 | Ginn |
| 2005/0107750 A1 | 5/2005 | Barongan |
| 2005/0107826 A1 | 5/2005 | Zhu et al. |
| 2005/0149116 A1 | 7/2005 | Edwards et al. |
| 2005/0149117 A1 | 7/2005 | Khosravi et al. |
| 2005/0228443 A1 | 10/2005 | Yassinzadeh |
| 2006/0100664 A1 | 5/2006 | Pai et al. |
| 2007/0020228 A1 | 1/2007 | Williams |
| 2007/0059350 A1 | 3/2007 | Kennedy et al. |
| 2007/0060895 A1 | 3/2007 | Sibbitt et al. |
| 2007/0270904 A1 | 11/2007 | Ginn |

* cited by examiner

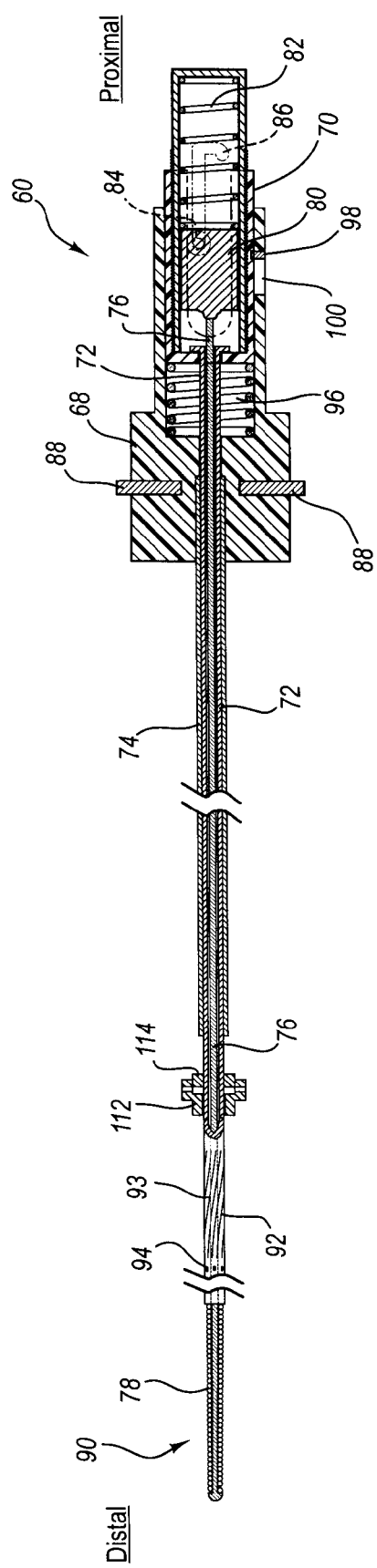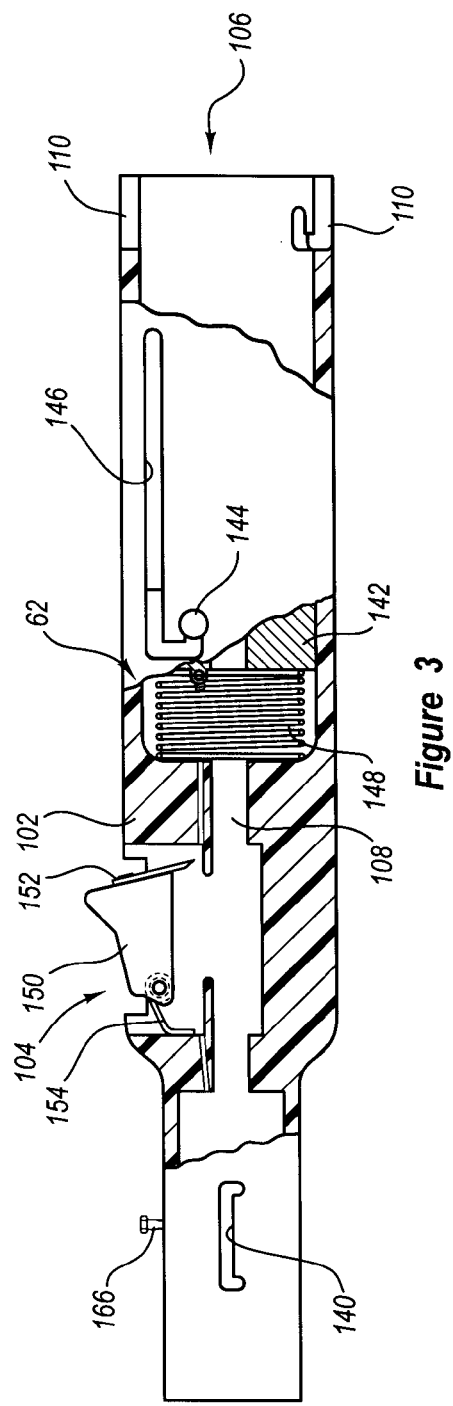
Figure 2
Figure 3

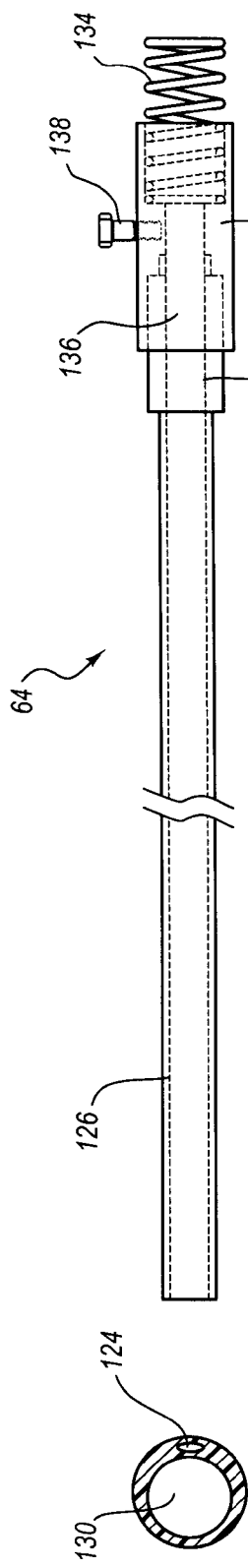
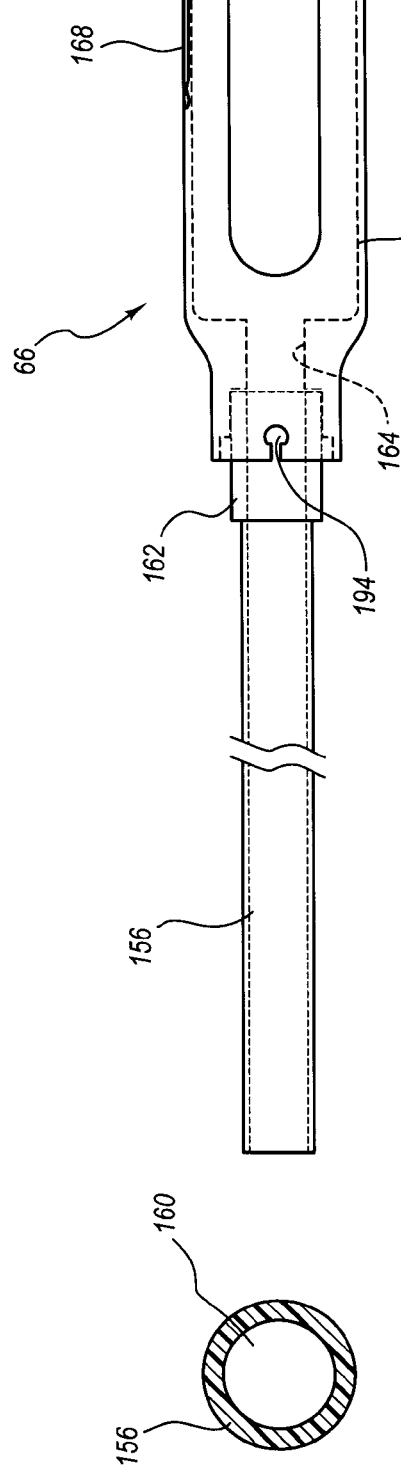
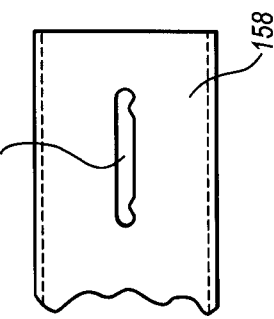
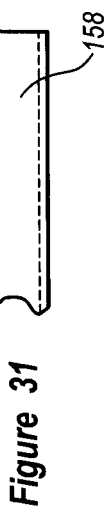
*Figure 4*
*Figure 5*
*Figure 6*
*Figure 7*
*Figure 31*

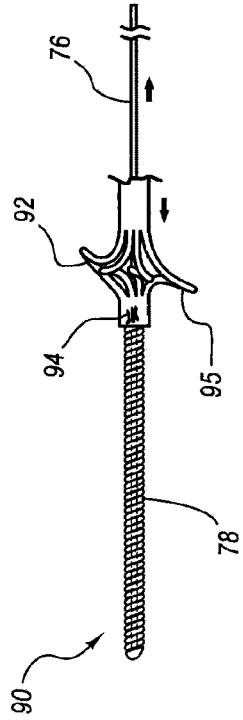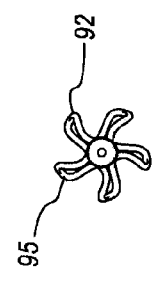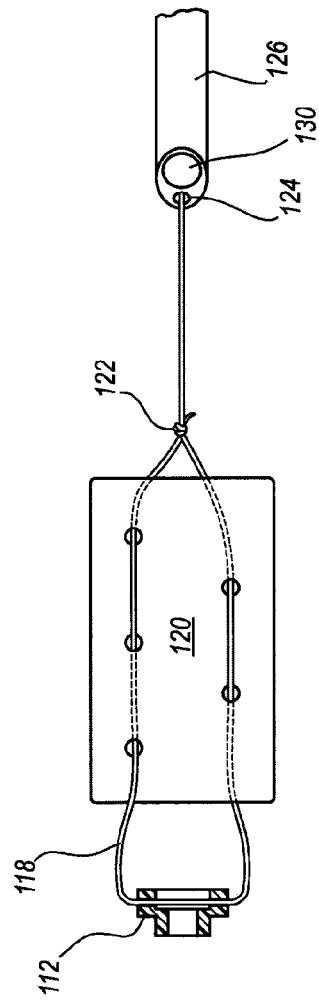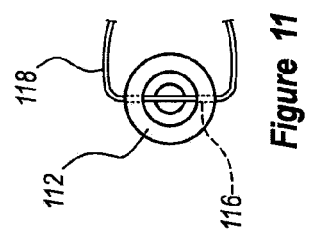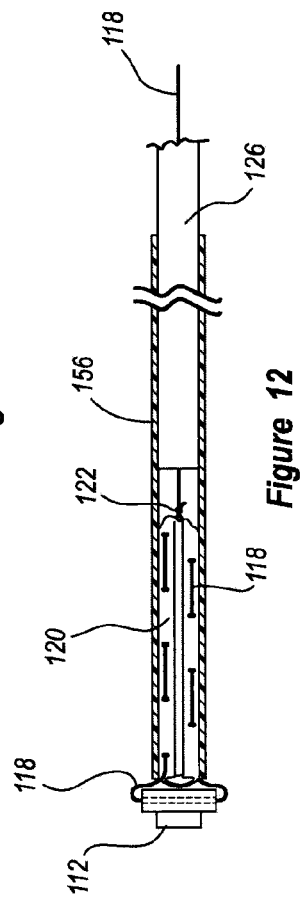

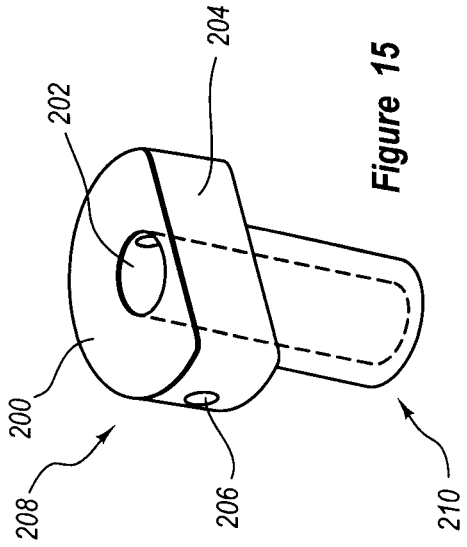
Figure 15
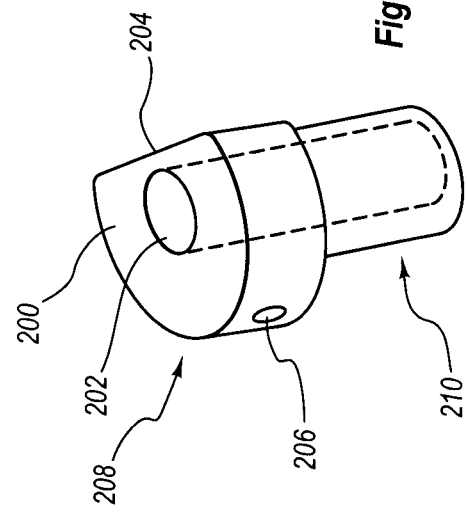
Figure 16
Figure 17
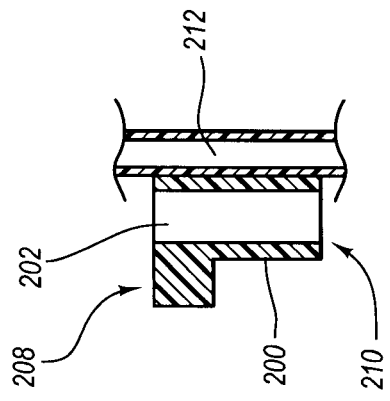
Figure 18
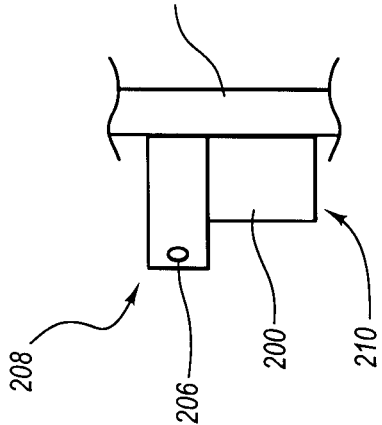
Figure 19
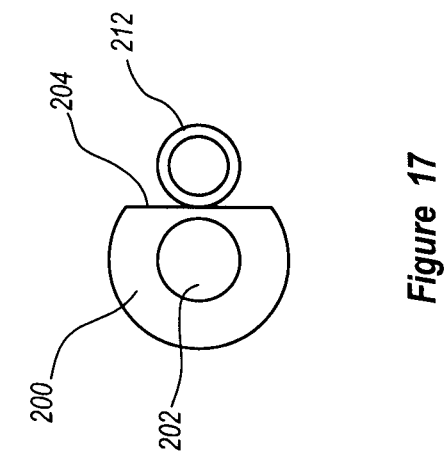

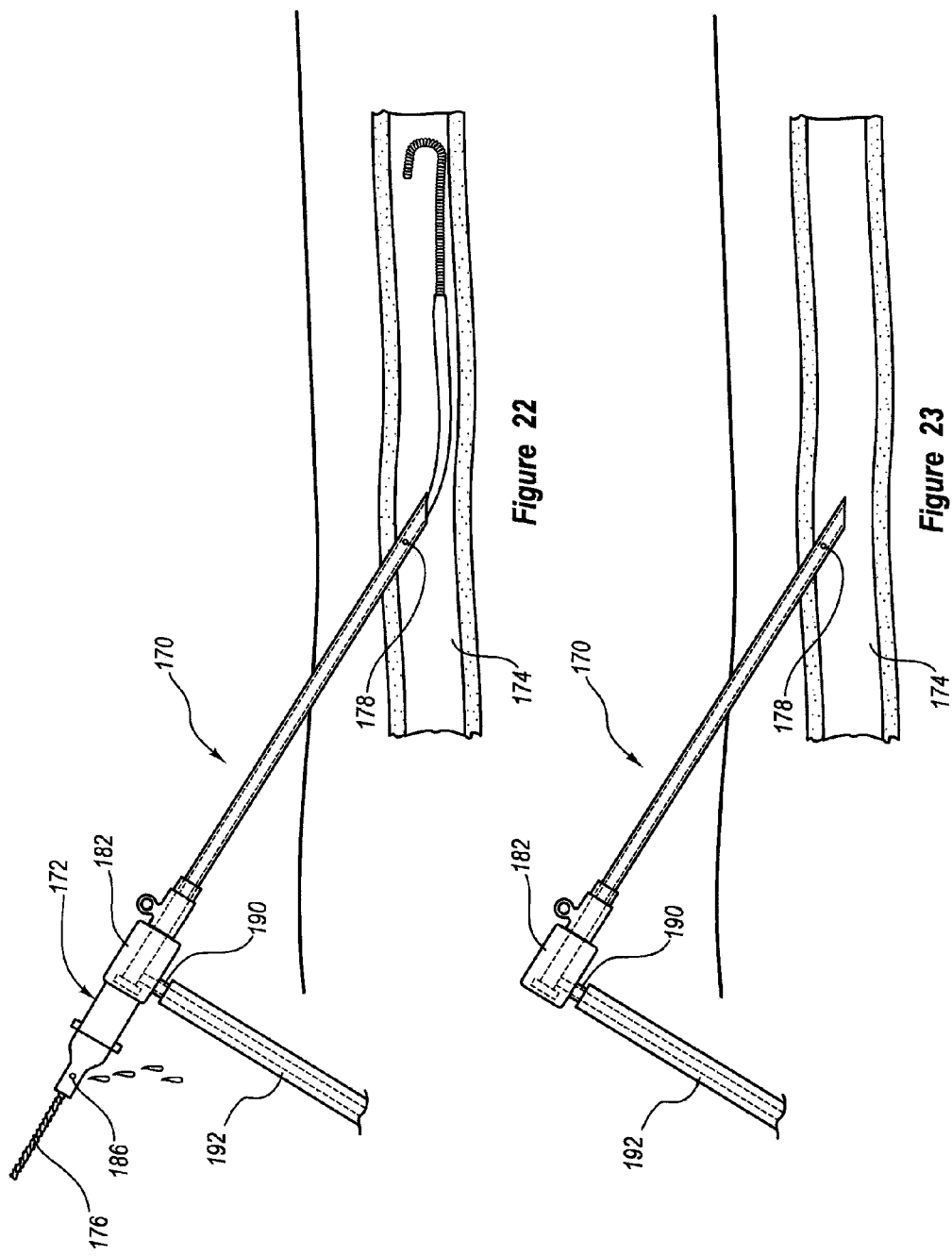

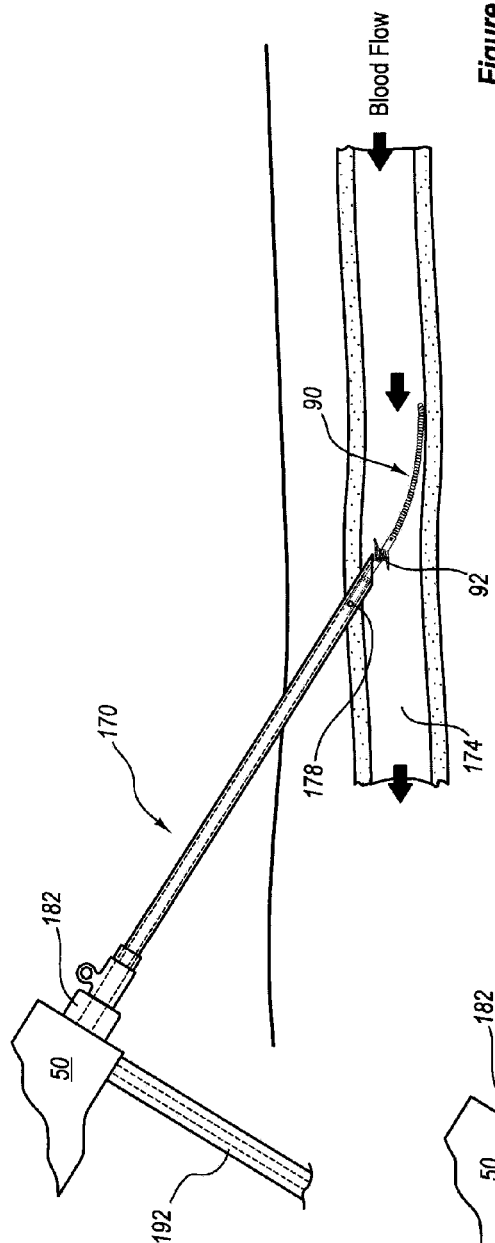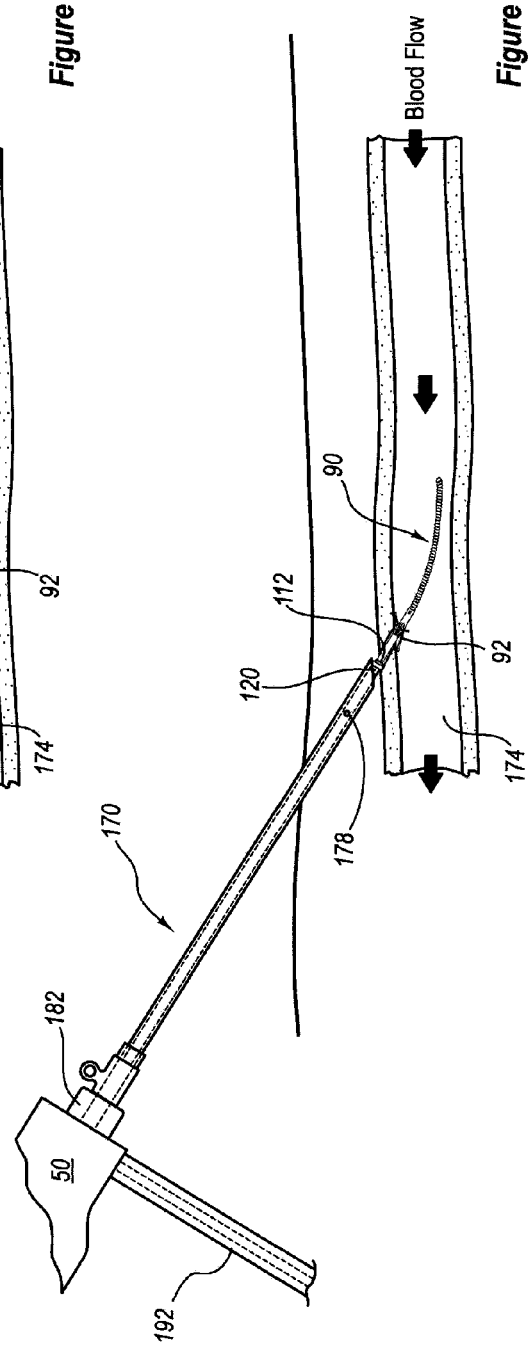

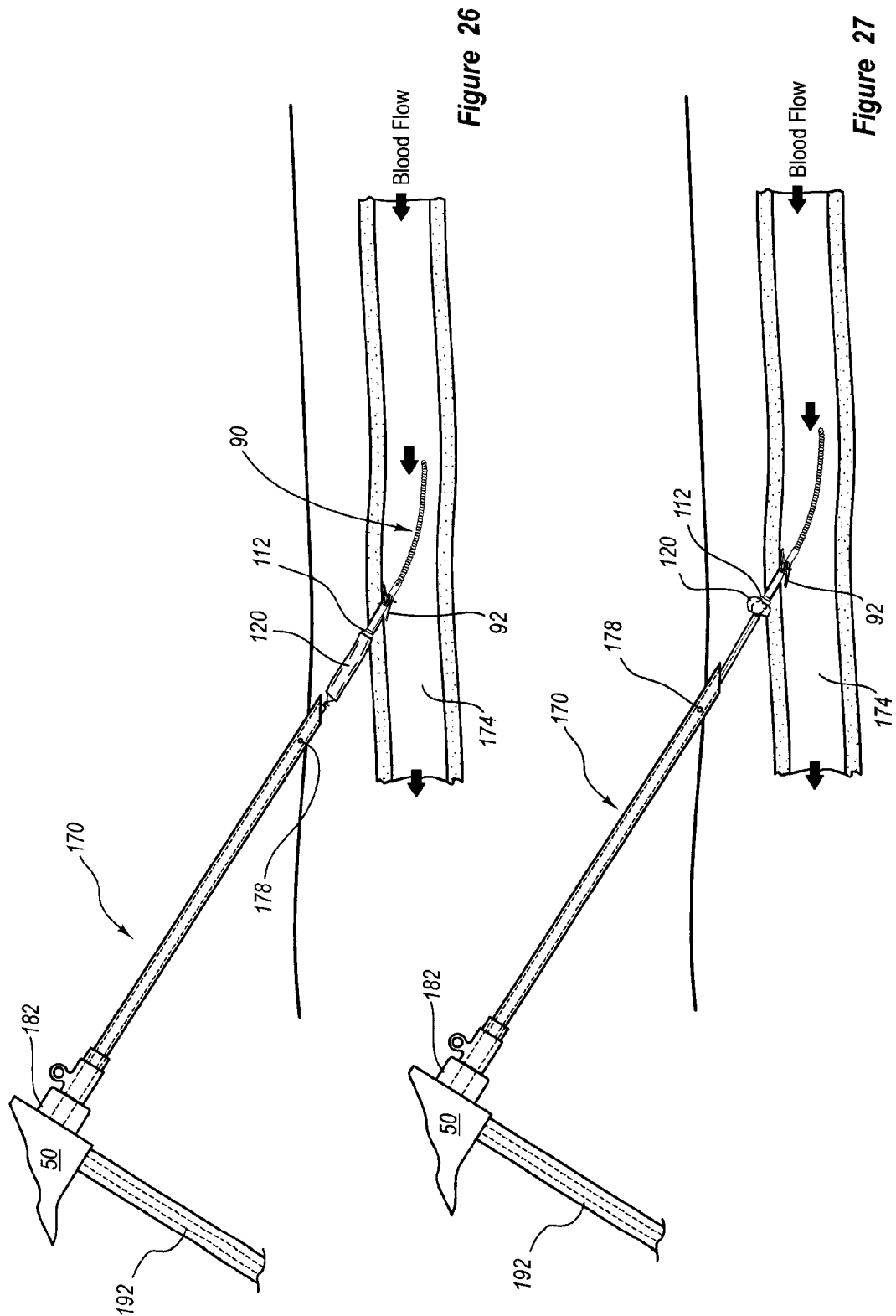

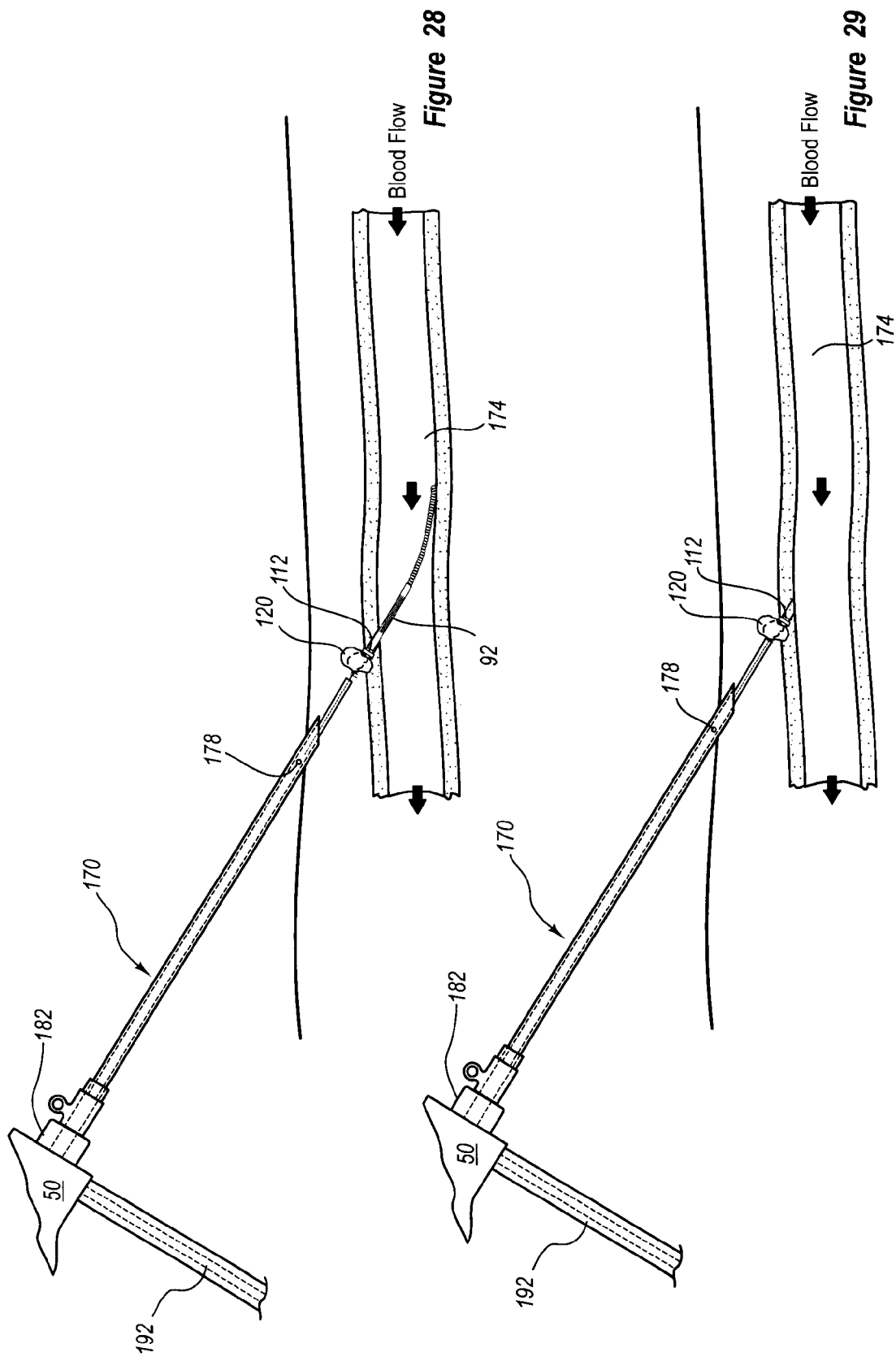

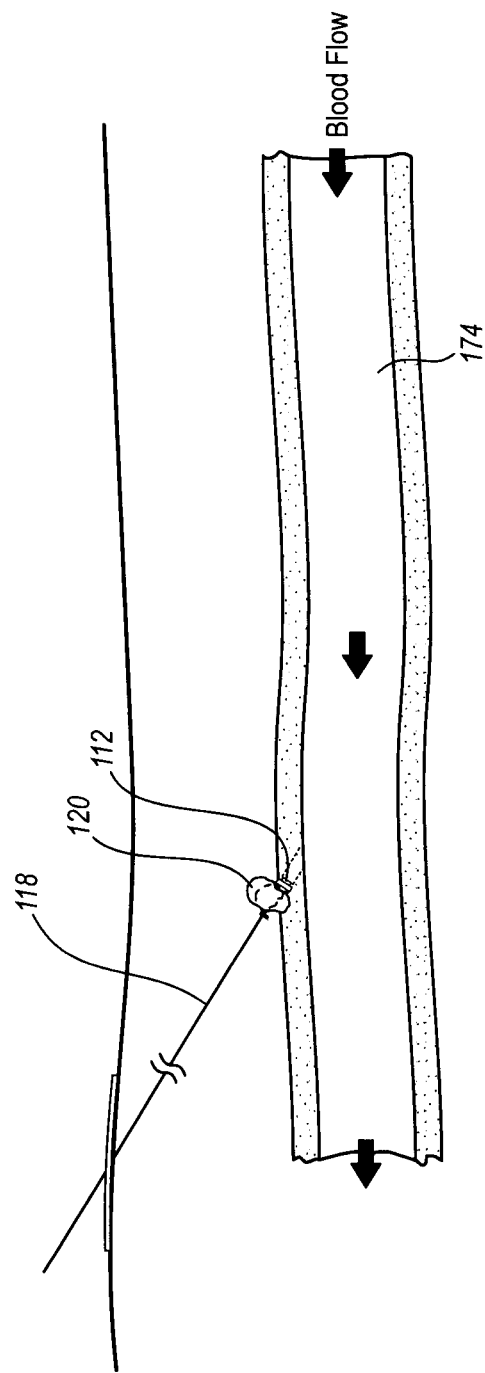

EXTRA-VASCULAR SEALING DEVICE AND METHOD

BACKGROUND

Catheter based diagnostic and interventional procedures such as angiograms, balloon angioplasty, stenting, atherectomy, thrombectomy, device placement, etc. are commonly employed to treat patients with vascular obstructions or other abnormalities accessible through the vasculature of the human body. Such interventions are less traumatic to the body than previous surgical interventions and therefore are growing in use.

To gain access to the vasculature, the Seldinger technique is commonly employed. This involves placing a small gauge hollow needle through the skin at about a 30 degree angle to intersect the desired vessel, commonly, but not always, the femoral artery in the groin area. The needle is known to have punctured the vessel wall when blood exits the needle at the proximal end. A guidewire is inserted through the needle into the vessel and the needle is removed. A dilator with a lumen sized to fit the guidewire has a leading tapered end and an outside diameter sized to fit closely in an introducer sheath placed over it. The introducer sheath size is selected (typically 5-8 Fr) to accommodate the catheters anticipated to be used in the procedure. The introducer sheath and tapered dilator are advanced together over the guidewire through the skin and into the vessel. The dilator and guidewire are then removed, since the vascular pathway from outside the body through the sheath and into the vessel have been established. A self sealing stretchable valve at the proximal end of the introducer sheath minimizes blood loss from the introducer sheath during the procedure.

Following the procedure and after all of the catheters and guidewires have been removed from the body, the introducer sheath is removed from the artery. Historically, this has been done by exerting manual pressure on the vessel upstream from the access site to lower blood pressure while the introducer sheath was removed. Once removed, manual pressure is applied directly to the skin above the access puncture for about thirty minutes to inhibit blood loss until the body's natural clotting process sealed the puncture. This technique is generally considered unsatisfactory because it is uncomfortable for the patient and requires a significant amount of nursing time.

Sealing the artery after sheath removal by manual compression is rapidly being replaced by medical devices designed to provide a vascular puncture seal in less than five minutes utilizing devices that are easy to use and operate by medical personnel. The devices range from mechanical suturing devices to collagen plugs, vascular clips, staples, and use of adhesives and sealants. These various approaches have had varying degrees of success and ease of use.

One or the more commonly used devices for closing vessel punctures achieves hemostasis at the vessel puncture site by closing the puncture with an absorbable intra-vessel (e.g., intra-arterial) anchor and an extra-vessel (e.g., extra-arterial) collagen sponge. The anchor and collagen are held together with a self tightening suture loop and slip knot, which, when tightened, sandwiches the puncture hole between the anchor and the collagen sponge. The device is easy to use and the bio-absorbable anchor, collagen and suture sandwich seals the vessel quickly, is more comfortable for the patient, saves valuable nurse time, and allows early patient ambulation.

Although such collagen devices can be highly effective, a substantial number of punctures in, for example, the femoral artery, may cause the patient to be ineligible to use such a device. Factors that may prevent use of this device include presence of peripheral vascular disease, poor needle stick location (too high or too low), or small vessel size which interferes with anchor placement and prevents proper seating of the anchor against the arterial wall.

In an effort to overcome some of these problems, vascular closure devices have been developed that deposit collagen outside the vessel with no component inside the vessel. Such devices may generally require, however, consistently placing the collagen near the arterial wall. Also, these devices may not allow the user to compress or tamp the collagen against the arterial wall due to the risk of inadvertently pushing the collagen into the vessel and resultant embolization.

Accordingly, it would be desirable to provide an improved vascular closure device or vascular sealing device that is easy to use, seals quickly and securely, and leaves no component in the blood vessel. A number of embodiments of such improved vascular closure devices are shown and described herein.

SUMMARY

Various embodiments of vascular closure devices are shown and described herein. The vascular closure devices are, generally speaking, hemostatic devices intended to stop bleeding by closing vascular access puncture sites following percutaneous diagnostic or therapeutic procedures. It should be appreciated that the vascular closure devices shown and described herein may be used to close any puncture in any blood vessel although the vascular closure devices are most commonly used to close arteriotomies. It should also be appreciated that the closure devices may be used to close punctures or holes in other bodily vessels.

The vascular closure devices provide for rapid hemostasis of vascular access puncture sites utilizing bio-absorbable, extra-vascular components positioned with reference to the vessel wall with no component left inside the vessel. The vascular closure devices may be considered extra-vascular closure devices because the devices do not leave any components in the blood vessel. In one embodiment, the vascular closure device may be configured to deploy an anchor and/or a sealing material outside of the blood vessel adjacent to the hole. In another embodiment, the vascular closure device may include a vessel locating member that is configured to assist the user in locating the blood vessel to ensure that the extra-vascular component(s) is placed properly adjacent to the hole in the blood vessel.

In one embodiment, the vascular closure device may include any one of the following: a vessel locator assembly, a carrier tube assembly, a tamper assembly, and a suture tightening assembly. The vascular closure device may also include an anchor, suture, and a sealing material such as collagen. The vascular closure device may include a handle having a plurality of actuation members for operating and controlling the device. The vessel locator assembly may include an atraumatic spring tip at the distal end and proximal to that, a vessel locating member that can be expanded or contracted using one or more of the actuation members on the handle. In one embodiment, the vessel locating member is a section of nitinol hypotube that is spiral cut to form a plurality of strut members that can expand outward and contract back inward. In another embodiment, the vessel locating member is a balloon that can be inflated with any suitable fluid such as saline solution, carbon dioxide, and the like.

Operation of the vascular closure device may be as follows. A closure sheath is initially inserted through the hole and into the blood vessel. Once the closure sheath is in place, the vascular closure device is inserted into the proximal end of the closure sheath and advanced until the vascular closure device is connected to the closure sheath. In one embodiment, the handle of the vascular closure device may be configured to connect to the proximal end of the closure sheath. At this point, the spring tip and the vessel locating member extend out of the distal tip of the closure sheath inside the blood vessel. The vessel locating member is expanded by operating one of the actuation members positioned on the handle. The closure sheath and the vascular closure device are withdrawn, proximally, until the user feels the vessel locating member contact the wall of the blood vessel. When contact has been made, the tip of the closure sheath is outside the blood vessel. An indicator included with the vascular closure device signals when the contact force of the vessel locating member and the wall of the blood vessel exceeds a safe amount to advise the user not to pull harder in the proximal direction.

After the vascular closure device is in position, the extra-vascular sealing components may be deployed to close the hole in the blood vessel. The position of the anchor and the vessel locating member is fixed relative to each other on the vascular closure device so that when the vessel locating member is in contact with the wall of the blood vessel, the anchor is positioned outside the hole in the blood vessel. A suture may be used to hold the anchor and the sealing material together. The suture may be configured to extend through a hole in the anchor and through a sealing material positioned proximal to the anchor within the carrier tube. One end of the suture may be formed into a slip knot near the proximal end of the collagen. The free end of the suture extends proximally through the vascular closure device and is coupled to the handle.

With the vessel locating member positioned against the inside surface of the blood vessel, the carrier tube is retracted. In one embodiment the carrier tube may be retracted by actuating one of the actuation members on the handle. Retracting the carrier tube exposes the anchor, suture, and sealing material to the puncture tract. The sealing material may be tamped against the anchor using the tamper assembly, and the suture may be tightened to hold the sealing material and the anchor together. In one embodiment, this suture may be tightened by actuating one or more of the actuation members on the handle.

After the anchor and the sealing material have been deployed, the vessel locating member may be contracted and removed from the blood vessel. In one embodiment, the vessel locating member may be contracted by actuating one of the actuation members on the handle. The vessel locator assembly of the vascular closure device can be detached and removed from the remainder of the vascular closure device. The carrier tube and the tamper assembly may hold the sealing material and the anchor in position as the vessel locator assembly is removed. The sealing material may be configured to expand to occupy the space where the now retracted vessel locator assembly used to be. Also, the sealing material may be configured to swell to seal the puncture. In one embodiment, a mechanical cutter on the handle may be activated to cut the suture free from the handle.

It should be appreciated that all of the components left in the patient are outside of the blood vessel and may be biodegradable. At this point, the remaining components of the vascular closure device as well as the closure sheath can be removed from the body and a bandage applied to the skin surface. The vascular closure device provides a number of advantages by eliminating the use of implanted intra vascular components. Also, the vascular closure device provides a consistent seal because the anchor and the sealing material can be tamped or compressed together and then held by the suture.

The foregoing and other features, utilities, and advantages of the subject matter described herein will be apparent from the following more particular description of certain embodiments as illustrated in the accompanying drawings.

DRAWINGS

FIG. 2 shows a partial cross-section of the vessel locator assembly of the vascular device.

FIG. 3 shows a handle body of the vascular closure device.

FIG. 4 shows the tamper assembly of the vascular closure device.

FIG. 5 shows a cross-sectional view of the tamper member from the tamper assembly shown in FIG. 4.

FIG. 6 shows a carrier tube assembly of the vascular closure device.

FIG. 7 shows a cross-sectional view of the carrier tube from the carrier tube assembly shown in FIG. 6.

FIG. 8 shows a side view of one embodiment of a vessel locating member in an expanded configuration.

FIG. 9 shows an end view of the vessel locating member from FIG. 8.

FIG. 10 shows an expanded view of an anchor, a sealing material, and a suture that may be included with the vascular closure device.

FIG. 11 shows an end view of the anchor from FIG. 10.

FIG. 12 shows a cross-sectional view of the anchor, sealing material, and suture positioned within the carrier tube.

FIGS. 15-16 show another embodiment of an anchor that can facilitate the use of blood-flash-back to determine the position of the anchor.

FIGS. 17-19 show various views of the anchor from FIGS. 15-16 and an accompanying blood-flash-back tube.

FIG. 22 shows the dilator assembly being used with the closure sheath to position the closure sheath in the blood vessel.

FIG. 23 shows the closure sheath after it has been positioned in the blood vessel.

FIG. 24 shows the vascular closure device inserted through the closure sheath into the blood vessel with a vessel locating member in an expanded configuration.

FIG. 25 shows the vascular closure device and the closure sheath retracted so that the expanded vessel locating member is against the interior wall of the blood vessel and the anchor is positioned adjacent to the exterior wall of the blood vessel.

FIG. 26 shows the vascular closure device with the carrier tube and closure sheath retracted to deploy the sealing material in the puncture tract.

FIG. 27 shows the sealing material from FIG. 26 being tamped against the anchor.

FIG. 28 shows the vessel locating member being in a contracted configuration.

FIG. 29 shows the vascular closure device after the vessel locator assembly has been removed. The tamper member is also shown holding the sealing material and the anchor in position as the vessel locator assembly is removed.

FIG. 30 shows the anchor, sealing material, and suture after the vascular closure device and the closure sheath have been removed. The anchor and sealing material are positioned outside of the blood vessel but adjacent to the hole in the blood vessel.

FIG. 31 shows a top view of the carrier tube assembly having a slot to receive a pin extending outward from the handle of the vascular closure device to allow the carrier tube assembly to move relative to the handle.

DETAILED DESCRIPTION

A number of embodiments of vascular closure devices are shown and described herein. The vascular closure devices may be used to close a hole or puncture in a blood vessel such as an arteriotomy. The vascular closure devices are hemostatic devices that may be used to stop bleeding from vascular puncture sites following percutaneous diagnostic or therapeutic procedures.

The vascular closure devices may be configured to deploy one or more bio-absorbable sealing materials outside of the blood vessel adjacent to the hole. The sealing material blocks the puncture tract and stops the bleeding. In one embodiment, the bio-absorbable components may swell to further block and seal the puncture tract. In another embodiment, the sealing material may be deployed with and coupled to another bio-absorbable component such as an anchor. Over time the bio-absorbable components are removed by the body's natural processes. The vascular closure devices may be considered extra-vascular closure devices because the devices do not leave any components in the blood vessel.

The success of an extra-vascular closure device depends on a number of factors. One factor that significantly impacts the ability of the vascular closure device to properly seal the hole in the blood vessel is the proper placement of the bio-absorbable components relative to the hole. If the bio-absorbable components are improperly positioned (e.g., too far away from the hole), a hematoma or other complication may arise.

Before describing the particular embodiments of the vascular closure devices, it should be appreciated that the features, advantages, characteristics, etc. described or shown in connection with one of the embodiments may be applied to or combined with any other embodiment to form an additional embodiment unless noted otherwise. Thus, the various embodiments may be modified in a variety of ways to produce many additional embodiments.

Figure 1:
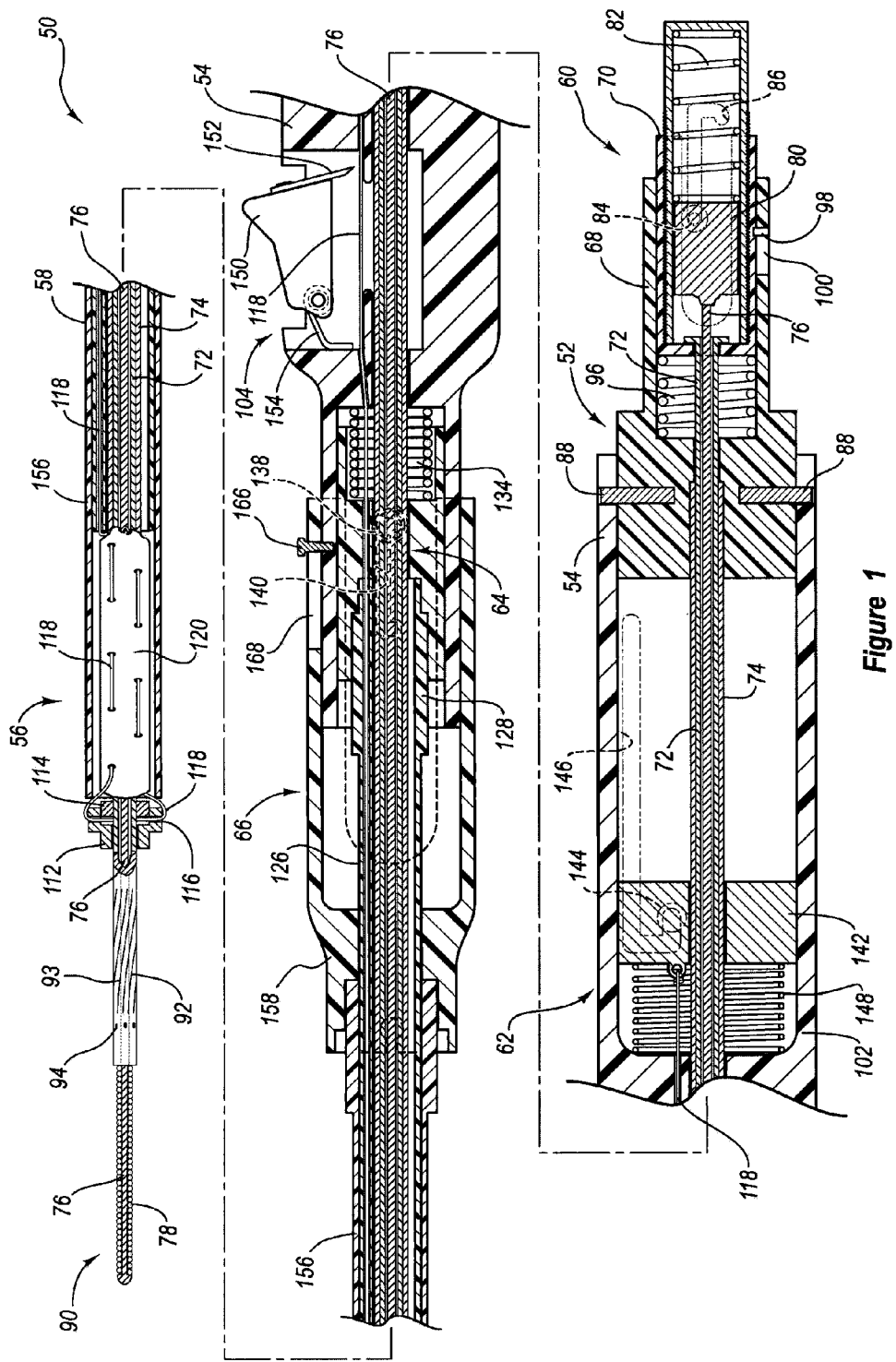
FIG. 1 shows the vascular closure device in an undeployed configuration.

FIG. 1 shows one embodiment of a vascular closure device 50 that may be used to close and/or seal a hole or puncture in a blood vessel such as an arteriotomy. The vascular closure device 50 includes a handle 54 positioned on a proximate side 52 of the vascular closure device 50 and an elongated or main body 58 positioned on a distal side 56 of the vascular closure device 50. The handle 54 allows the user to grip and operate the vascular closure device 50. The elongated body 58 is configured to be inserted into the puncture tract (usually by way of a sheath) to close the hole in the blood vessel.

The vascular closure device 50 also includes a vessel locator assembly 60, a suture tightening assembly 62, a tamper assembly 64, and a carrier tube assembly 66. These assemblies 60, 62, 64, 66, when coupled together as shown in FIG. 1, form the handle 54 and the elongated body 58. Each of these assemblies is described in greater detail as follows. Before proceeding further, it should be noted that for purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

Turning to FIG. 2, one embodiment of the vessel locator assembly 60 is shown. The vessel locator assembly 60 is generally used to determine the position of the blood vessel as part of the process of closing the hole. The vessel locator assembly 60 includes a sleeve, housing, or body 68, a housing or body 70 that moves lengthwise within the housing 68, a first tube 72, a second tube 74, and a core wire or guide wire 76. A plunger or movable member 80 and a spring or biasing member 82 are positioned inside the housing 70. An actuation member or pin 84 extends outward from the plunger 80 and through a slot 86 in the housing 70. The actuation member 84 can be used to move the plunger 80 back and forth in the housing 70.

The core wire 76 is coupled to a distal end of the plunger 80. The core wire 76 extends from the plunger 80 through the first tube 72 to a distal end 90 of the vascular closure device 50. The first tube 72 is coupled to a distal end of the housing 70 and extends through the second tube 74 towards the distal end 90 of the vascular closure device 50.

A spring 78 (e.g., coiled stainless steel spring) is coupled to the distal end of the first tube 72 and surrounds the core wire 76. The spring 78 may be coupled to the first tube 72 using any suitable fastening mechanism or technique such as, for example, brazing, soldering, or epoxy adhesive. The distal end of the core wire 76 is tapered or reduced in diameter to make the distal end 90 of the vascular closure device 50 more flexible. The distal end of the core wire 76 is coupled to the distal end of the spring 78. Both the core wire 76 and the spring 78 are configured to be atraumatic to prevent the distal end 90 of the vascular closure device 50 from puncturing or damaging the blood vessel.

The first tube 72 and the second tube 74 may be coupled to the plunger 80 and the housing 70, respectively, using any suitable fastening mechanism or technique. Also, the core wire 76 may be coupled to the spring 78 using any suitable fastening mechanism or technique. In one embodiment, these components may be coupled together by brazing, soldering, or with adhesives.

The vessel locator assembly 60 also includes a vessel locating member 92. The vessel locating member 92 is positioned at the distal end of the first tube 72. When the elongated body 56 is inserted into a blood vessel, the vessel locating member 92 is positioned inside the blood vessel. In the embodiment shown in FIG. 2, the vessel locating member 92 includes a plurality of strut members 93 formed by making a series of cuts around the first tube 72 in a spiral pattern. The cuts may be made using a laser or any other suitable device or technique.

Turning to FIGS. 8-9, the vessel locating member 92 may be configured to move between the expanded configuration shown in FIGS. 8-9 and the contracted configuration shown in FIGS. 1-2. This allows the vessel locating member 92 to be inserted into the blood vessel, expanded, and then moved into contact with the interior wall of the blood vessel adjacent to the hole.

The vessel locating member 92 moves between the expanded configuration and the contracted configuration as follows. The core wire 76 is coupled to the first tube 72 at a position 94 that is distal to the vessel locating member 92. The vessel locating member 92 may be expanded by moving the actuation member 84 (see FIG. 2) proximally which causes the plunger 80 and the core wire 76 to also move proximally. The slot 86 includes a hook portion that receives the actuation member 84 to hold the actuation member 84 in a locked position to hold the vessel locating member 92 in the expanded configuration. The movement of the core wire 76 in the proximal direction exerts a compressive force on the first tube 72 that causes the strut members 93 to deflect outwardly. In one embodiment, the strut members 93 bow and twist as they deflect outwardly. The result, shown in FIG. 9, is that the strut members 93 form a plurality of petal shaped vessel locators 95 that extend radially outward from the first tube 72.

The vessel locating member 92 may be moved back to the contracted configuration shown in FIGS. 1-2 by moving the actuation member 84 distally to its original position. The spring 82 may by used to provide additional force to make it easier to move the actuation member 84, and therefore the plunger 80 and the core wire 76, back in the distal direction. The movement of the core wire 76 in the distal direction exerts a tension force on the first tube 72 that causes the strut members 93 to straighten and contract or collapse so that the strut members 93 are again in line with the first tube 72.

In one embodiment, the cuts in the wall of the first tube 72 may be configured so that the vessel locators 95 of the vessel locating member 92 form a plane that is not perpendicular to the first tube 72 as shown in FIG. 8. This may be desirable to create more uniform contact between the vessel locating member 92 and the interior wall of the blood vessel. Since the puncture tract is usually at a 30-45 degree angle relative to the blood vessel (see, e.g., FIGS. 22-30), the plane formed by the vessel locating member 92 may also be at an approximately 30-45 degree angle relative to the first tube 72 (see FIG. 8). When the vessel locating member 92 is in the blood vessel, the vessel locating member 92 may be roughly parallel to the interior wall of the blood vessel just before the vessel locating member 92 contacts the interior wall.

It should be appreciated that the configuration of the vessel locating member 92 can be modified in any of a number of ways. For example, the vessel locating member 92 may be configured to be perpendicular to the first tube 72. In another embodiment, the vessel locating member 92 may include an inflatable balloon.

The second tube 74 may be provided to stiffen the elongated body 58 of the vascular closure device 50 and to provide a passageway for the first tube 72. It should be appreciated that the first tube 72, the second tube 74, and any of the other components of the vessel locator assembly 60 may be made of any suitable material such as metal, plastics, or composites. Since the vascular closure device 50 is a medical device, the materials used may also be medical grade (medical grade metals, plastics, or composites). In one embodiment, the first tube 72, the second tube 74, and the core wire 76 may be made of metals such as stainless steel or memory shape metals such as nitinol, and the like. In another embodiment, the first tube 72 may be made of a memory shape material such as nitinol (e.g., nitinol hypotube) to allow the vessel locating member 92 to repeatedly expand and contract. In yet another embodiment, the second tube 74 may be a stainless steel tube to provide additional strength, and the core wire 76 may be a stainless steel wire.

Referring to FIGS. 1-2, the vascular closure device 50 is configured to indicate when the vessel locating member 92 is in contact with the interior wall of the blood vessel. One problem associated with locating the wall of the blood vessel is that the user may be unable to feel when the vessel locating member 92 has contacted the wall of the blood vessel. The user may continue to pull on the vascular closure device 50 causing it to distort and bend until it passes through the hole in the blood vessel or the expanded vessel locating member 92 may tear through the hole in the wall of the blood vessel causing additional injury to the patient.

The housing 70 and the sleeve 68 are configured to signal to the user when the expanded vessel locating member 92 is positioned against the interior wall of the blood vessel. The housing 70 is positioned to move lengthwise in the sleeve 68. The first tube 72 is coupled to the housing 70 so that when the vessel locating member 92 contacts the interior wall of the blood vessel, the housing 70 moves distally in the sleeve 68. A spring 96 is positioned between the housing 70 and the sleeve 68 to bias the housing 70 in the proximal direction. The spring 96 is configured to compress only when the vessel locating member 92 has contacted the interior wall of the blood vessel.

An indicator pin 98 extends outward from the housing 70 and travels in a slot 100 in the sleeve 68. The indicator pin 98 prevents the spring 96 from biasing the housing 70 out the proximal end of the sleeve 68. As the spring 96 is compressed, the indicator pin 98 moves distally in the slot 100. In operation, the user can pull back on the vascular closure device 50 while watching the indicator pin 98. When the indicator pin 98 begins to move distally in the slot 100, the user knows that the vessel locating member 92 is positioned against the interior wall of the blood vessel.

It should be appreciated that numerous other methods may be used to signal the user that the vessel locating member 92 is positioned against the interior wall of the blood vessel. The signal may be visual, auditory, or any other suitable type of signal. In one embodiment, the vascular closure device 50 may be configured to emit a beep to alert the user that the vessel locating member 92 is positioned against the interior wall of the blood vessel.

Referring to FIG. 3, the handle 54 includes a handle body 102 that forms much of the assembled handle 54. The handle body 102 includes the suture tightening assembly 62 and a suture cutting assembly 104. The vessel locator assembly 60 is configured to be coupled to the proximate end 106 of the handle body 102. This is done by inserting the tubes 72, 74 through a central bore 108 of the handle body 102 until the distal end of the sleeve 68 extends into the proximate end 106 of the handle body 102. The handle body 102 includes two U-shaped slots 110 that are configured to receive the pins 88 on the sleeve 68. One leg portion of the U-shaped slots 110 is open to the proximal end 106 of the handle body 102 while the other leg portion is shorter and not open to the proximal end 106. The vessel locator assembly 60 is coupled to the handle body 102 by moving the pins 88 into the longer leg portions of the slots 110, rotating the sleeve 68, and then withdrawing the sleeve 68 slightly to seat the pins 88 in the shorter leg portions of the slots 110. It should be appreciated that any suitable method may be used to couple the vessel locator assembly 60 to the handle body 102.

Returning to FIG. 2, an anchor or support member 112 is carried by the first tube 72. The anchor 112 is positioned a predetermined distance in the proximal direction from the vessel locating member 92. The distance between the anchor 112 and the vessel locating member 92 is selected so that when the vessel locating member 92 is positioned against the interior wall of the blood vessel, the anchor 112 is positioned just outside of the hole in the blood vessel.

The anchor 112 is configured to slide on and off the first tube 72. A stop sleeve 114 is fixed to the first tube 72 to prevent the anchor 112 from sliding too far in the proximal direction. The stop sleeve 114 forces the anchor 112 to move in the distal direction when the first tube 72 moves in the distal direction.

Another embodiment of an anchor 200 is shown in FIGS. 16-19. The anchor 200 may be used in place of the anchor 112. The anchor 200 has a lumen 202 that travels lengthwise through the anchor 200 and is sized to fit on the second tube 74 of the vessel locator assembly 60. The anchor 200 also includes a distal end 208, a proximal end 210, a first side 204, and a hole 206 that extends transversely through the distal end 208. The hole 206 is configured to receive the suture 118 in a manner similar to that shown for anchor 112.

The first side 204 of the anchor 200 is shaped to allow a tube 212 to be positioned adjacent to the anchor 200 and extend slightly past the distal end 208 of the anchor 200. The tube 212 extends from the anchor 200 back to a location near the handle 52 of the vascular closure device 50. The tube 212 is positioned to provide a blood-flash-back signal to the user when the anchor 200 is in position near the blood vessel. When the tube 212 is just positioned far enough into the blood vessel for blood to flash back to the user, the user knows that the anchor 200 is correctly positioned. In this way, the tube 212 functions as a vessel locating member.

In one embodiment, the anchor 200 and tube 212 may be used with the vascular closure device 50 of FIG. 1 with some slight modifications to route the tube 212 up to the handle 52. In this embodiment, the vessel locating member 92 may be used to initially find the wall of the blood vessel and the tube 212 may be used to fine tune the position of the anchor 200 relative to the wall. In another embodiment, the vascular closure device 50 may use only the tube 212 to locate the blood vessel and position the anchor 200. In this situation, the tube 212 may function as the vessel locating member 92.

Figure 21:
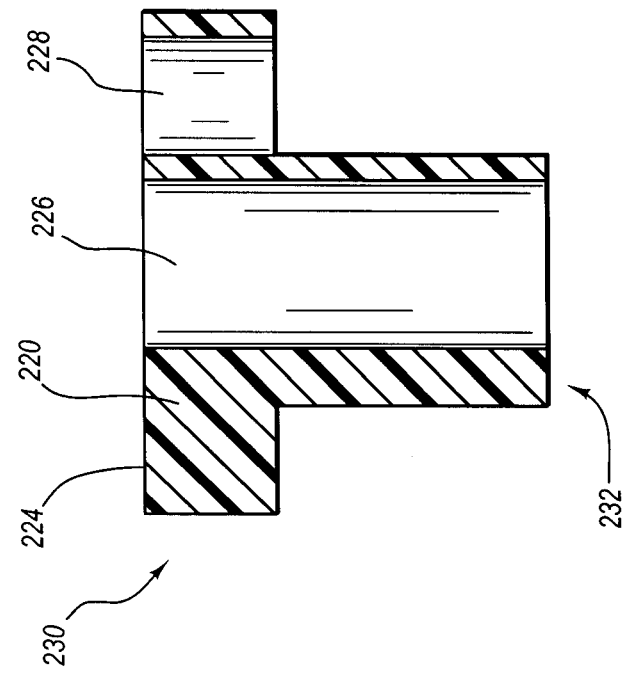
FIGS. 20-21 show another embodiment of an anchor that can facilitate the use of blood-flash-back to determine the position of the anchor.
Figure 20:
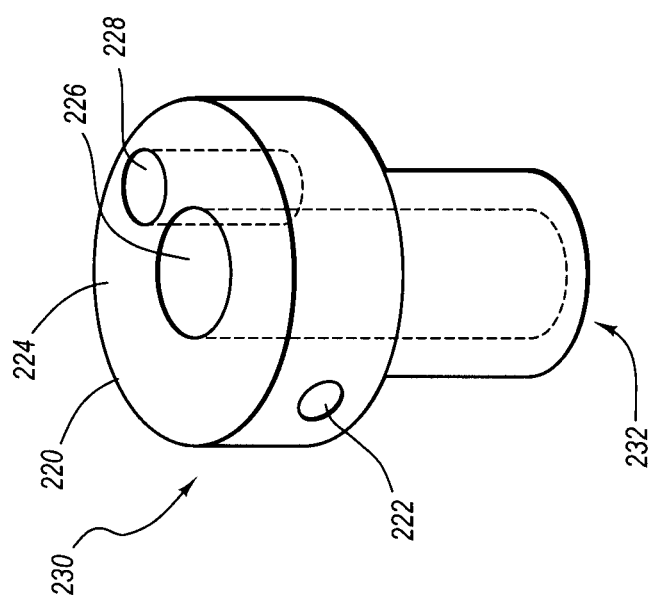

FIGS. 20-21 show another embodiment of an anchor 220 that includes a lumen or hole 226 that extends lengthwise through the anchor 220, a distal face 224, a distal end 230, a lumen or hole 228 that is positioned parallel to the first lumen 226, a proximal end 232, and a lumen or hole 222 that extends transversely through the anchor 220 at the distal end 230. The lumen 222 is configured to receive the suture 118. The lumen 226 is configured to receive the second tube 74 from the vascular locator assembly 60. The lumen 228 is configured to be coupled to a tube that extends back to the handle 52 of the vascular closure device 50 to provide a blood-flash-back capability. In principle, the anchor 220 operates similarly to the anchor 200 except that the tube 212 is replaced by the lumen 228, which is an integral part of the anchor 220.

Referring to FIGS. 4-5, the tamper assembly 64 is shown. The tamper assembly 64 is provided to allow the user to tamp or compress a sealing material 120 (see FIG. 1) against the anchor 112. The tamping action serves to push the sealing material 120 radially outward against the walls of the puncture tract. This helps to hold the sealing material 120 and the anchor 112 in place as well as to further seal the puncture tract to prevent blood from leaking out.

The tamper assembly 64 includes a tamper member or tamper tube 126 coupled to a tamper body or sleeve 128. The tamper member 126 includes a first lumen or hole 130 and a second lumen or hole 124 both of which extend lengthwise through the tamper member 126. The first lumen 130 is sized to slidably receive the second tube 74 from the vessel locator assembly 60. The second lumen 124 is sized to receive a suture or filament 118 (see FIG. 1). A heat shrink strain relief 132 surrounds a proximal portion of the tamper member 126. The heat shrink strain relief 132 and the tamper member 126 are coupled to the tamper body 128. Tamper body 128 has a through bore or passage 136 that is sized to receive the second tube 74 from the vessel locator assembly 60. Also, the tamper body 128 includes a cavity at the proximal end that is sized to receive a spring or biasing member 134.

The tamper assembly 64 also includes an actuation member or pin 138 that extends outward from the tamper body 128. The actuation member 138 is configured to be threaded into the tamper body 128 and extend outward through the slot 140 of the handle body 102 (see FIG. 3). The actuation member 138 is initially located at the proximal end of the slot 140 as shown in FIG. 1. In this position, the spring 134 is fully compressed between the tamper body 128 and the handle body 102. Moving the actuation member 138 laterally releases the spring force and displaces the tamper member 126 which then pushes the sealing material 120 into contact with the anchor 112. As shown in FIG. 1, the tamper assembly 64 is coupled to the handle body 102 by inserting the tamper body 128 into a distal cavity in the handle body 102. The actuation member 138 and slot 140 hold the tamper assembly 64 and the handle body 102 together.

Referring back to FIG. 1, it can be seen that the sealing material 120 is positioned proximal to the anchor 112. The vascular closure device 50 is configured to deploy the sealing material 120 adjacent to the hole in the blood vessel with the anchor 112 positioned between the hole in the blood vessel and the sealing material 120. In one embodiment, the sealing material 120 may be configured to swell when it contacts blood to further assist in closing the hole. The sealing material 120 may be any suitable material such as collagen.

The anchor 112 also has a transverse hole or lumen 116 sized to receive the suture 118 as shown in FIGS. 10-11. The suture 118 extends through the anchor 112 and the sealing material 120. In the embodiment shown in FIGS. 1, 10, and 12, the suture 118 passes through multiple holes in the sealing material 120 in a distal direction, through the transverse hole 116 in the anchor 112, and back through more holes in the sealing material 120 in a proximal direction. A slip knot 122 (see FIG. 10) on one end of the suture 118 is positioned above (or proximal of) the sealing material 120 so that a loop is formed around the anchor 112 and the sealing material 120. As shown in FIG. 1, the other end of the suture 118 extends proximally from the sealing material 120 through the second lumen 124 in the tamper member 126, through the tamper body 128, through the spring 134, adjacent to the suture cutting assembly 104, and ending at a cylinder 142 where the suture 118 is anchored. It should be appreciated that although the suture 118 is shown being tied to a loop of the cylinder 142, any suitable technique may be used to couple the suture 118 to the cylinder 142.

Referring to FIG. 1, the suture tightening assembly 62 is shown. The suture tightening assembly 62 is configured to exert the appropriate amount of force on the suture 118 to hold the anchor 112 and the sealing material 120 together without pulling the anchor 112 and/or the sealing material 120 proximally in the puncture tract. In other embodiments, the suture 118 may be tightened manually by the user pulling on the suture 118. However, manually tightening the suture 118 may be less desirable because it may result in pulling the anchor 112 and/or the sealing material 120 proximally down the puncture tract and away from the hole in the blood vessel.

The suture tightening assembly 62 includes the cylinder 142, which has a central bore or passage that is sized to slidably receive the second tube 74 from the vessel locator assembly 60. An actuation member or pin 144 extends outward from the cylinder 142 into a slot 146 in the handle body 102. A spring or biasing member 148 is positioned between the handle body 102 and the distal end of the cylinder 142. The slot 146 has a positive stop position at the distal end to hold the cylinder 142 in place against the force of the spring 148. As shown in FIGS. 1 and 3, when the actuation member 144 is locked at the distal end of the slot 146, the spring 148 is compressed and no tension is placed on the suture 118. If the actuation member 144 is moved laterally the cylinder 142 is pushed or biased in the proximal direction by the spring 148. This results in the cylinder 142 pulling the suture 118 in the proximal direction. This tightens the slip knot 122 and compresses the sealing material 120 against the anchor 112 outside of the hole in the blood vessel. It should be noted that typically the suture 118 is tightened in this manner after the sealing material 120 has been tamped with the tamper assembly 64.

The suture cutting assembly 104 may be used to cut the suture 118 after it has been tightened. Referring again to FIG. 3, the suture cutting assembly 104 includes a button 150 and a blade 152. The button 150 is pivotably coupled to the handle body 102 and biased upward by a spring or biasing member 154. At the appropriate time, the user can cut the suture 118 simply by pressing down on the button 150, which causes the blade 152 to move downward and cut the suture 118.

Turning now to FIGS. 6-7 and 31, the carrier tube assembly 66 is shown. The carrier tube assembly 66 includes a carrier tube 156 coupled to a carrier tube body 158. The carrier tube assembly is configured to fit over the distal end of the handle body 102 and enclose the suture 118 and the sealing material 120 as shown in FIG. 12. The carrier tube 156 has a lumen 160 that extends lengthwise through the carrier tube 156. The lumen 160 is sized to slidably receive the tamper member 126 therein. The lumen 160 also encloses the suture 118 and sealing material 120. A strain relief heat shrink 162 surrounds the proximal portion of the carrier tube 156. The strain relief 162 and the carrier tube 156 are inserted within a cavity at the distal end of the carrier tube body 158 to couple the components together. The carrier tube body 158 includes a through bore or passage 164 that is sized to slidingly receive the tamper member 126.

The carrier tube body 158 is configured to slide over the outside of the distal end of the handle body 102. A pin 166 (see FIGS. 1 and 3) is inserted through a slot 168 in the carrier tube body 158 and threadably received by a hole in the handle body 102. The slot 168 is shown in greater detail in the top view of the carrier tube body in FIG. 31. The carrier tube assembly 66 can slide lengthwise along the distal end of the handle body 102. The slot 168 limits the lengthwise movement of the carrier tube assembly 66. The carrier tube body 158 is initially as far distal as the slot 168 will allow. In this position, the carrier tube 156 covers the sealing material 120 as shown in FIGS. 1 and 12. When the sealing material 120 is deployed, the carrier tube assembly 66 is moved proximally as far as the slot 168 will allow. This moves the carrier tube 156 proximally to expose the sealing material 120 inside the puncture tract just prior to tamping it and tightening the suture 118.

Figure 13:
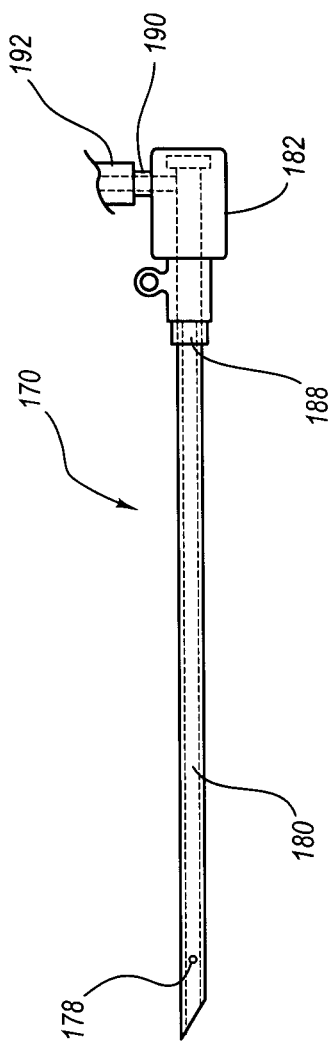
FIG. 13 shows a closure sheath that may be used to allow the vascular closure device to access the blood vessel.
Figure 14:
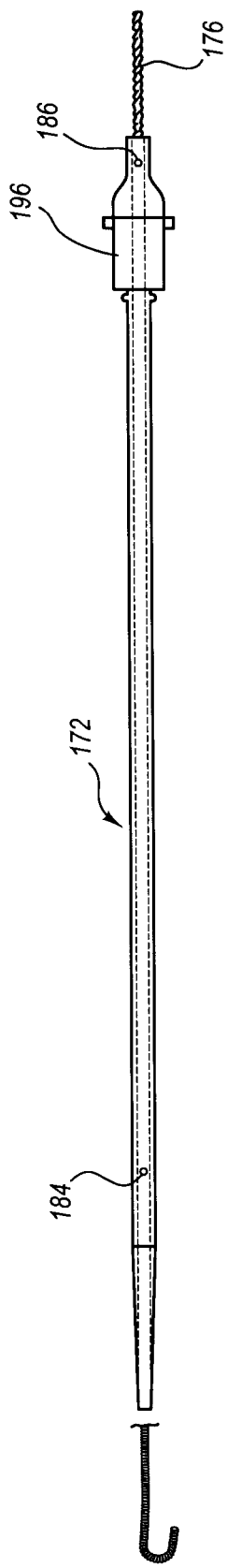
FIG. 14 shows a dilator assembly and accompanying guide wire that may be used to help position the closure sheath in the blood vessel.

FIGS. 13 and 14 show a closure sheath assembly 170 and a closure dilator 172. The closure sheath assembly 170 is an introducer sized and configured to be used with the vascular closure device 50. The closure dilator 172 is used to properly position the closure sheath assembly 170 in the puncture tract. The configuration of the closure sheath assembly 170 and the closure dilator 172 is explained in greater detail in connection with the description of the following method of closing a hole in a blood vessel.

A method of closing a hole in a blood vessel 174 using the vascular closure device 50 is described in connection with FIGS. 22-30. Initially, the procedural sheath is exchanged for the closure sheath assembly 170. This is done by placing a guidewire 176 through the procedural sheath and into the blood vessel 174. The procedural sheath is then withdrawn from the body while holding digital pressure on the blood vessel 174, upstream from the sheath, and while holding the guidewire 176 in place. Next, the closure dilator 172, shown in FIG. 14, is placed within the closure sheath assembly 170 and the distal tapered end of the closure dilator 172 is backloaded onto the guidewire 176. The closure dilator 172 and the closure sheath assembly 170 are advanced together distally over the guidewire 176, through the puncture or tissue tract, and into the blood vessel 174 (see FIG. 22).

The closure sheath assembly 170 includes a closure sheath 180 and a connector 182. The closure sheath 180 has a side hole 178 near the distal end of the closure sheath 180. The side hole 178 is a prescribed distance from the distal end of the closure sheath 180. When the closure dilator 172 is positioned in the closure sheath 180, the side hole 178 aligns with a distal side hole 184 in the closure dilator 172. The closure dilator 172 also has a proximal side hole 186 at the proximal end of the closure dilator 172 that is in fluid communication with the distal side hole 184. In one embodiment, the side holes 184, 186 may be fluidly connected by way of a dedicated lumen or bore. In another embodiment, the side holes 184, 186 may be fluidly connected by the central lumen of the closure dilator 172 that the guidewire 176 is positioned in.

The side holes 178, 184, 186 are provided to allow blood to flash back when the closure sheath 180 is correctly positioned in the blood vessel 174. Once blood flows out the proximal side hole 186 of the closure dilator 172, as shown in FIG. 22, the user knows to pull the closure sheath 180 in a proximal direction until the blood flow just stops. The closure sheath 180 is now placed in the correct position to continue the procedure. The next step is to withdraw the closure dilator 172 and the guidewire 176 while holding the closure sheath assembly 170 in place (see FIG. 23).

The closure sheath 180 is sized to slidably receive the vascular closure device 50 therein. The distal end of the closure sheath 180 has a taper cut so that the tip will align with the lengthwise axis of the blood vessel 174 when the closure sheath 180 is inserted through the puncture tract at an angle of about 30-45 degrees to the vessel axis. Referring again to FIG. 13, a strain relief 188 made from heat shrink tubing surrounds the closure sheath 180 at the proximal end where both are coupled to the connector 182. A side port 190 and tubing 192 are in fluid communication with the lumen of the closure sheath 180. The side port 190 is also sized to be securely received by a slot 194 in the carrier tube body 158, shown in FIG. 6, to hold these components together during the closure procedure.

The closure dilator 172 has an outside diameter that is sized to snugly fit within the closure sheath 180. The closure dilator 172 includes a connector 196 (see FIG. 14) that is configured to lightly snap together with the connector 182 of the closure sheath assembly 170. This allows the closure sheath assembly 170 and the closure dilator 172 to move together as one unit. The closure dilator 172 has a lumen sized to receive the guidewire 176.

After the closure sheath assembly 170 is in place as shown in FIG. 23, the vascular closure device 50 is introduced into the proximal end of the closure sheath assembly 170. The vascular closure device 50 is advanced until the side port 190 from the closure sheath assembly 170 mates and locks into the slot 194 of the carrier tube assembly 66 (see FIG. 24). In this position, the distal end 90 of the vascular closure device 50 extends out of the distal end of the closure sheath 180 and into the blood vessel 174. It should be noted that the vessel locating member 92 is also inside the blood vessel 174. The actuation member 84 from the vessel locator assembly 60 is moved proximally into the locked position. This action pulls the core wire 76 relative to the first tube 72 and expands the vessel locating member 92 radially outward as shown in FIG. 24. The closure sheath assembly 170 and the vascular closure device 50 are drawn away from the patient until the vessel locating member 92 contacts the vessel wall at the puncture site. As previous explained, the user will know when this happens by watching for movement from the indicator pin 98 (see FIG. 1). Movement of the indicator pin 98 signals that the vessel locating member 92 is in contact with the wall of the blood vessel 174 and further force is not desirable. In this position (see FIG. 25), the distal end of the closure sheath 180 and the anchor 112 are positioned just outside of the vessel wall.

Now that the vessel locating member 92 and the anchor 112 are in position, the closure sheath 180 and the carrier tube 156 are withdrawn to expose the sealing material 120 to the tissue puncture tract. This is accomplished by holding the handle body 102 steady while pulling proximately on the connector 182 from the closure sheath 180. The pin 166 remains fixed in position while the carrier tube body 158 slides proximally until the pin 166 reaches the distal end of the slot 168. The sealing material, which may include a collagen sponge, is now exposed to the puncture tract and starts to absorb blood and swell. This is shown in FIG. 26.

Now that the sealing material 120 has been deployed, the next step is to tamp it with the tamper assembly 64. This is accomplished by holding the handle body 102 in position and moving the actuation member 138 laterally from the locked position into the slot 140. The spring 134 biases the tamper member 126 distally into the sealing material 120. The tamper member 126 compresses the sealing material 120 against the anchor 112, the wall of the blood vessel 174, and the vessel locating member 92. The vessel locating member 92 prevents the sealing material 120 from being pushed inside the blood vessel 174. FIG. 27 shows the sealing material 120 after it has been tamped.

The suture 118 is tightened to hold the sealing material 120 in a compressed state. The suture is tightened by holding the handle body 102 steady and moving the actuation member 144 from the locked position to a position where the spring 148 can bias the cylinder 142 in a proximal direction. The cylinder 142 is coupled to the suture 118 so that as the cylinder 142 moves proximally, the suture is also pulled proximally and the slip knot 122 is tightened. At this point, the sealing material 120 and the anchor 112 have been deployed and the only remaining steps are to remove the closure sheath assembly 170 and the vascular closure device 50.

The first step in removing the vascular closure device 50 is to contract or collapse the vessel locating member 92 and remove the vessel locator assembly 60 from the vascular closure device 50. The vessel locating member 92 is contracted by moving the actuation member 84 distally while holding the handle body 102 steady. The spring 82 helps to move the actuation member 84 distally. The vessel locating member 92 is shown in the contracted configuration in FIG. 28. At this point, the vessel locator assembly 60 may be separated from the handle body 102 by rotating the sleeve 68 to release the pins 88 from the locked position of slots 110 in the handle body 102. The vessel locator assembly 60 is removed by pulling it out the proximal end of the handle body 102. As the first tube 72 passes through the sealing material 120, the sealing material 120 swells to fill the gap where the first tube 72 used to be. The hole in the blood vessel 174 is now sealed by clotting action and the swelling of the sealing material 120 against the puncture tract walls. The anchor 112 and the sealing material 120 are not disturbed by the removal of the vessel locator assembly 60 since the first tube 72 and the coiled spring 78 are smaller than the lumen through the anchor 112 (see FIG. 29).

The suture 118 is cut by pressing down on the button 150, which pushes the blade 152 into the suture 118. Once the suture 118 is cut the remaining components of the closure sheath assembly 170 and the vascular closure device 50 may be withdrawn proximally from the patient to leave only the suture 118 protruding from the skin as shown in FIG. 30. The suture 118 is cut below the skin by the operator compressing the skin and severing the suture 118 at a point below the surface of the skin. The closure procedure is now complete and the sealing material 120, suture 118, and the anchor 112 will be absorbed by the body in about 90 days or less.

It should be appreciated that the embodiments disclosed have many components and the methods described have many steps for operation and use. It is anticipated that the number of components and steps could be altered considerably (e.g., remove the second tube 74, etc.) without departing from the broad scope of what is described herein. For example the steps of tamping and tensioning the suture 118 could be combined into one step.

ILLUSTRATIVE EMBODIMENTS

Reference is made in the following to a number of illustrative embodiments of the subject matter described herein. The following embodiments illustrate only a few selected embodiments that may include the various features, characteristics, and advantages of the subject matter as presently described. Accordingly, the following embodiments should not be considered as being comprehensive of all of the possible embodiments. Also, features and characteristics of one embodiment may and should be interpreted to equally apply to other embodiments or be used in combination with any number of other features from the various embodiments to provide further additional embodiments, which may describe subject matter having a scope that varies (e.g., broader, etc.) from the particular embodiments explained below. Accordingly, any combination of any of the subject matter described herein is contemplated.

According to one embodiment, a method of closing a hole in a blood vessel comprises: positioning an anchor outside of the hole in the blood vessel; and positioning a sealing material adjacent to the anchor, the sealing material also being outside of the blood vessel. The anchor may be positioned between the sealing material and the hole in the blood vessel. The method may comprise locating a wall of the blood vessel adjacent to the hole. Locating the wall of the blood vessel may include inserting a vessel locating member through the hole in the blood vessel, expanding the vessel locating member, and moving the vessel locating member into contact with the wall of the blood vessel. The method may comprise compressing the sealing material and the anchor together. The method may comprise compressing the sealing material and the anchor together using a tamper member. The method may comprise holding the sealing material and the anchor together using a suture. The sealing material may include collagen.

According to another embodiment, a method of closing a hole in a blood vessel comprises: locating a wall of the blood vessel adjacent to the hole; positioning an anchor outside of the blood vessel and adjacent to the hole; positioning a sealing material adjacent to the anchor, the sealing material also being outside of the blood vessel; and compressing the sealing material and the anchor together. Locating the wall of the blood vessel may include inserting a vessel locating member through the hole in the blood vessel, expanding the vessel locating member, and moving the vessel locating member into contact with the wall of the blood vessel. The vessel locating member may include a tube having a wall with a plurality of cuts in it, the wall of the tube being configured to expand where the plurality of cuts are located when the tube is compressed. The vessel locating member may include a balloon. Compressing the sealing material and the anchor together may include tamping the sealing material towards the anchor. The method may comprise holding the sealing material and the anchor together using a suture. The wall of the blood vessel may be located using a vascular closure device capable of signaling when the wall has been located. Locating the wall of the blood vessel may include inserting a vessel locating member through the hole in the blood vessel, expanding the vessel locating member, and moving the vessel locating member into contact with the wall of the blood vessel; compressing the sealing material and the anchor together may include tamping the sealing material towards the anchor; and the sealing material and the anchor may be held together with a suture.

According to another embodiment, a vascular closure device comprises: a vessel locating member configured to be inserted through a hole in a blood vessel to locate the position of a wall of the blood vessel that is adjacent to the hole; an anchor configured to be deployed outside of the blood vessel adjacent to the hole; a sealing material configured to be deployed adjacent to the anchor and outside of the blood vessel; and a suture configured to hold the anchor and the sealing material together when the anchor and the sealing material are deployed to close the hole in the blood vessel. The vessel locating member may be configured to move between an expanded configuration and a contracted configuration. The sealing material may include collagen. The vessel locating member may include a tube having a wall with a plurality of cuts in it, the wall of the tube being configured to expand where the plurality of cuts are located when the tube is compressed. The vessel locating member may include a balloon. The suture may be configured to tighten a predetermined amount to hold the anchor and the sealing material together. The vascular closure device may comprise a tamper member configured to move the sealing material toward the anchor. The vascular closure device may comprise an indicator that signals when the vessel locating member is positioned adjacent to the wall of the blood vessel.

According to another embodiment, a vascular closure device comprises: a vessel locating member configured to locate a wall of a blood vessel that is adjacent to a hole in the blood vessel; and an anchor configured to be deployed outside of the blood vessel adjacent to the hole in the blood vessel; wherein the vascular closure device is configured so that the anchor and the vessel locating member are positioned near each other so that when the vessel locating member is in contact with an interior surface of the wall of the blood vessel, the anchor is adjacent to the wall on the outside of the blood vessel. The vessel locating member may be configured to move between an expanded configuration to allow the vessel locating member to contact the interior surface of the wall of the blood vessel and a contracted configuration to allow the vessel locating member to pass through the hole in the blood vessel. The sealing material may include collagen. The vessel locating member may include a tube having a wall with a plurality of cuts in it, the wall of the tube being configured to expand where the plurality of cuts are located when the tube is compressed. The vessel locating member may include a balloon. The vascular closure device may comprise a sealing material configured to be deployed adjacent to the anchor. The vascular closure device may comprise a suture configured to hold the sealing material and the anchor together. The vascular closure device may comprise a tamper member configured to move the sealing material toward the anchor. The vascular closure device may comprise an indicator that signals when the vessel locating member is positioned adjacent to the wall of the blood vessel.

According to another embodiment, an extra-vascular closure device for closing puncture tracts from the surface of the skin through tissue into a vessel following a percutaneous diagnostic or therapeutic procedure comprises: an anchor adjacent the outside vessel wall at the arteriotomy; a mass of collagen adjacent the anchor in the proximal direction; and a length of suture affixing the collagen to the anchor. The anchor location may be a predetermined distance from the inner wall of the vessel at the arteriotomy. The inner wall of the vessel may be located by expandable and retractable struts or petals operable from outside the body. A visual indicator may assist in locating the vessel wall. The retractable struts or petals may be formed from a portion of nitinol hypotube having multiple spiral cuts through the wall, about the circumference, that radial expand upon compression of the hypotube and that contract upon release of the compression force. The radial expanded struts may form loops in a plane cross wise to the avis of the hypotube. The suture may pass through the anchor and collagen in a loop and is secured by a slip knot.

The terms recited in the claims should be given their ordinary and customary meaning. The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A vascular closure device comprising:
   a vessel locating member configured to be inserted through a hole in a blood vessel and expandable to locate the position of a wall of the blood vessel that is adjacent to the hole;
   an anchor configured to be deployed outside of the blood vessel adjacent to the hole, the anchor having a distal end portion and a proximal end portion when deployed;
   a sealing material configured to be deployed adjacent to and proximal of the anchor and outside of the blood vessel when the vessel locating member is positioned within the vessel and the anchor and sealing material are deployed; and
   a suture connected to the anchor, the suture configured to hold the anchor and the sealing material together when the anchor and the sealing material are deployed to close the hole in the blood vessel;
   wherein the vessel locating member is retractable through the deployed anchor and sealing material, the vessel locating member being positioned distal of the distal end portion of the anchor when the vessel locating member is positioned within the blood vessel, and the sealing material being positioned proximal of the proximal end portion of the anchor when the anchor and sealing material are deployed.

2. The vascular closure device of claim 1 wherein the vessel locating member is configured to move between an expanded configuration and a contracted configuration.

3. The vascular closure device of claim 1 wherein the sealing material includes collagen.

4. The vascular closure device of claim 1 wherein the vessel locating member includes a tube having a wall with a plurality of cuts in it, the wall of the tube being configured to expand where the plurality of cuts are located when the tube is compressed.

5. The vascular closure device of claim 1 wherein the vessel locating member includes a balloon.

6. The vascular closure device of claim 1 wherein the suture is configured to tighten a predetermined amount to hold the anchor and the sealing material together.

7. The vascular closure device of claim 1 comprising a tamper member configured to move the sealing material toward the anchor.

8. The vascular closure device of claim 1 comprising an indicator that signals when the vessel locating member is positioned adjacent to the wall of the blood vessel.

9. The vascular closure device of claim 1 wherein the suture is positioned outside of the vessel.

10. The vascular closure device of claim 1, wherein the anchor and sealing material are separate pieces and deployed independent of each other.

11. A vascular closure device comprising:
    a vessel locating member configured to expand within a vessel to locate an internal wall of a blood vessel that is adjacent to a hole in the blood vessel;
    an anchor configured to be deployed outside of the blood vessel adjacent to the hole in the blood vessel, the anchor having a distal end portion and a proximal end portion when deployed;
    a sealing material configured to be deployed adjacent to the anchor; and a suture configured to hold the sealing material and the anchor together; wherein the vascular closure device is configured so that the distal end portion of the deployed anchor and the vessel locating member are positioned near each other so that when the vessel locating member is in contact with an interior surface of the wall of the blood vessel, the distal end portion of the anchor is adjacent to the wall on the outside of the blood vessel;
    wherein the vessel locating member is retractable through the deployed anchor.

12. The vascular closure device of claim 11 wherein the vessel locating member is configured to move between an expanded configuration to allow the vessel locating member to contact the interior surface of the wall of the blood vessel and a contracted configuration to allow the vessel locating member to pass through the hole in the blood vessel.

13. The vascular closure device of claim 11 wherein the sealing material includes collagen.

14. The vascular closure device of claim 11 wherein the vessel locating member includes a tube having a wall with a plurality of cuts in it, the wall of the tube being configured to expand where the plurality of cuts are located when the tube is compressed.

15. The vascular closure device of claim 11 wherein the vessel locating member includes a balloon.

16. The vascular closure device of claim 11 comprising a tamper member configured to move the sealing material toward the anchor.

17. The vascular closure device of claim 11 comprising an indicator that signals when the vessel locating member is positioned adjacent to the wall of the blood vessel.

18. The vascular closure device of claim 11 wherein the vessel locating member is retractable through the deployed sealing material.

* * * * *